United States Patent [19]

Flatland

[11] 4,053,983
[45] Oct. 18, 1977

[54] PROPHYLACTIC ANGLE HEAD FOR USE WITH A DENTAL HANDPIECE

[76] Inventor: Lloyd P. Flatland, 15 Quisisana Drive, Kentfield, Calif. 94904

[21] Appl. No.: 679,734

[22] Filed: Apr. 23, 1976

[51] Int. Cl.² .............................................. A61C 1/10
[52] U.S. Cl. ...................................................... 32/27
[58] Field of Search ..................................... 32/27, 58

[56] References Cited

U.S. PATENT DOCUMENTS

| 1,198,628 | 9/1916 | Ebenreiter | 32/27 |
| 1,838,982 | 12/1931 | Angell | 32/27 |
| 3,798,777 | 3/1974 | Reiter | 32/32 |

Primary Examiner—Robert Peshock
Attorney, Agent, or Firm—Lothrop & West

[57] ABSTRACT

A prophylactic angle head for a dental handpiece having a driver in a threaded casing has a housing made up of an upper housing shell and a lower housing shell. The shells have faces meeting on a common plane. When put together the shells define an approximately spherical interior chamber having an opening to the outside and define a tube in communication with the chamber. The threaded casing engages matching threads on the housing shells to hold them together and to assemble them to the driving handpiece. A driver in the handpiece casing is coupled to a drive shaft in the housing. A bearing sleeve carries the drive shaft and is snugly seated between the two shells and assists in holding them against movement relative to each other. A bevel gear on the end of the drive shaft meshes with another bevel gear on an elongated hub and mounted for rotation on a hard, tungsten carbide pin seated in the upper shell and extending along an axis normal to that of the drive shaft. The hub extends toward the opening and is internally threaded to receive a dental tool.

5 Claims, 3 Drawing Figures

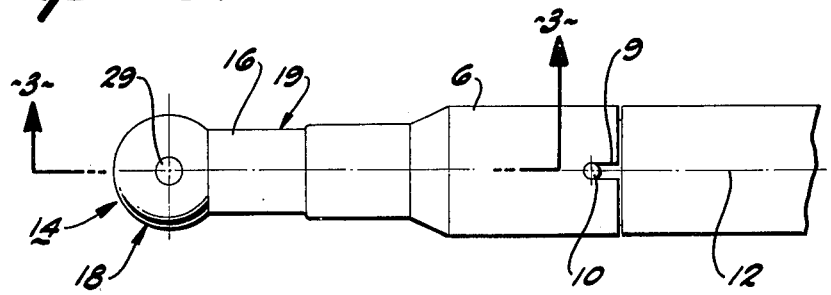
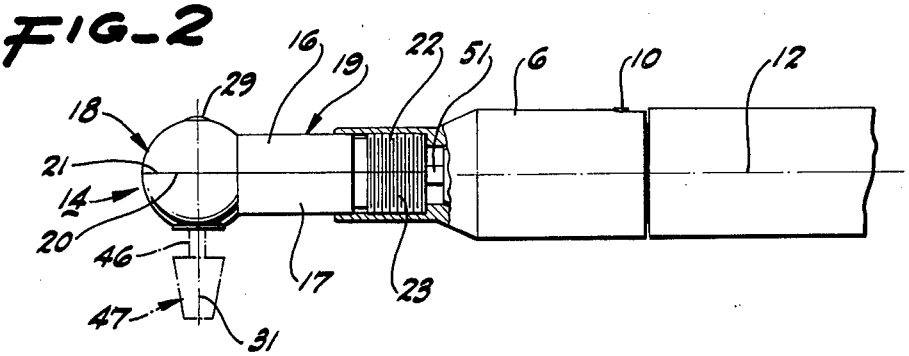
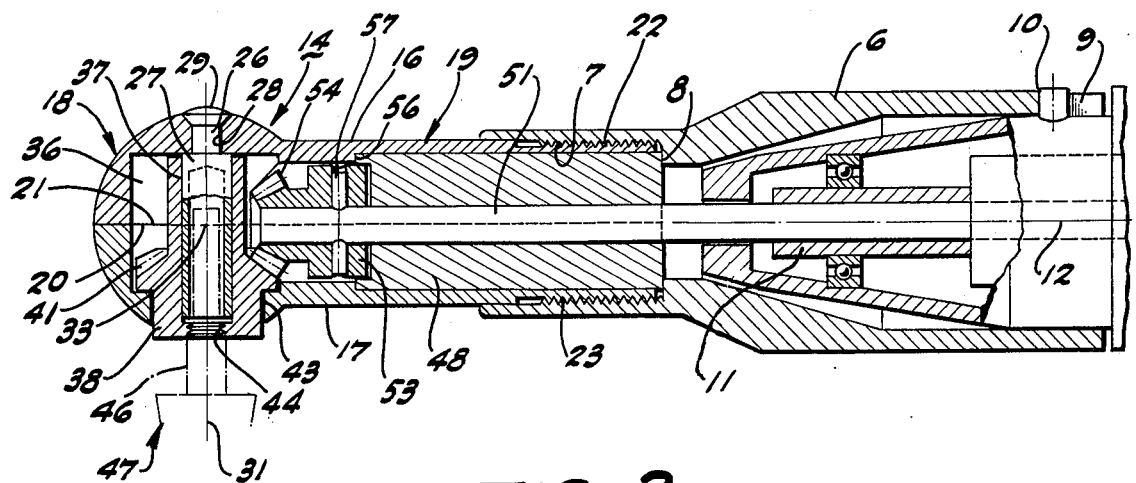

PROPHYLACTIC ANGLE HEAD FOR USE WITH A DENTAL HANDPIECE

For use by a dentist or dental assistant or hygienist in cleaning teeth and like operations, there is provided a so-called prophylactic angle handpiece head or "prophy angle" that can be attached to a straight handpiece of the usual sort. Normally such a straight handpiece has a casing enclosing a rotating, axially extending driver, and the casing is designed to receive a working attachment, such as a prophy angle head. The prophy angle head has a relatively difficult role in that it must operate under substantial load and must operate well and long even when considerable abrasive material and the like is present. The prophy angle head is inclusive of an angle drive for best use. It must be relatively cheap as well as effective, since such handpieces are intended to be discarded from time to time as the wear rate is relatively great and the bearings and comparable structures at best have a relatively short life.

It is therefore an object of the invention to provide a highly effective prophy angle head adapted for attachment to a straight handpiece and having an internal construction that is quite satisfactory as to bearing life and is capable of operating under relatively abrasive surroundings.

Another object of the invention is to provide a prophy angle head that is simple enough and can be economically enough manufactured so that after a relatively short time of use it can economically be discarded and replaced.

Another object of the invention is to provide a relatively inexpensive prophy angle head in which the bearings are relatively well protected and can in any event be changed or altered easily.

A further object of the invention is to provide a prophy angle head that can quickly and easily be disassembled and assembled, either for cleaning and servicing or for replacement of interior units.

Another object of the invention is to provide a prophy angle head that can be assembled without tools and when assembled maintains correct positioning and alignment.

Another object of the invention is to provide a generally improved prophy angle head.

Other objects, together with the foregoing, are attained in the embodiment of the invention described in the accompanying description and illustrated in the accompanying drawings, in which:

FIG. 1 is a top plan view of a prophylactic angle head assembled with a straight driver handpiece;

FIG. 2 is a side elevation of the device of FIG. 1; and

FIG. 3 is a cross-section through a portion of the structure shown in FIG. 1, the plane of section being indicated by the line 3—3 of FIG. 1.

While the prophy angle head can be variously mounted and employed, it has with considerable success been embodied as shown herein. In this representative instance there is made available a prophy angle head having an end section 6 with internal threads 7 ending at an internal shoulder 8. The end section has an aliging notch 9 adapted to engage a pin 10 or screw on the nose cone of the handpiece. Within the handpiece is a power driven collet 11 or chuck rotatable about a longitudinal axis 12.

Pursuant to the invention a housing 14 is provided. This is made up of an upper housing shell 16 and a lower housing shell 17. These shells include a generally spherical or first end portion 18 and a communicating, tubular shank portion 19. The upper shell 16 on a lower face has a planar surface 20, whereas the lower shell 17 has a planar upper surface 21. The arrangement is such that when the shells are positioned with the planar surfaces 20 and 21 in abutment, the so-formed housing 14 can be assembled symmetrically with the planar surfaces 20 and 21 on the axis 12. The shells are held in assembled location partly by engagement of the threads 7 with external threads 22 on the upper shell and 23 on the lower shell.

Within the upper shell 16 there is provided a hollow journal pin 26 having a shoulder 27. The pin extends through an opening 28 in the upper shell and is held in position by an enlarged or riveted cap 29. The journal pin 26 extends along an axis 31 at right angles to or normal to the axis 12 and intersects such axis on a center 33 that is also the center of the outer spherical portion of the shells. There is also provided a generally circular-cylindrical compartment 36.

Preferably, the journal pin is made of or is provided with a surface of a relatively hard, long-lasting material such as tungsten carbide. Designed to rotate on the pin is a bearing 37 inserted into or forming part of a gear hub 38. The gear hub near one end is connected to a bevel gear 41. At one end the hub 38 thrusts endwise against the upper shell 16 and at the other end thrusts against the lower shell 17. The hub 38 is extended along the axis 31 to approach very close to or even extend through an opening 43 in the lower housing shell 17. The interior of the lower portion of the hub 38 is hollow and is provided with threads 44 to receive the threaded shank 46 of an appropriate dental tool 46 such as a prophylactic cup. If the cup shank is long above the threaded portion, it extends into the interior of the hollow pin 26.

As part of the aligning and driving mechanism, the two internally tubular portions 19 of the housing shells 16 and 17 enclose a bearing sleeve 48 symmetrical with the axis 12. The sleeve makes a snug fit and helps hold the shells against relative movement. The bearing sleeve is also designed to support a drive shaft 51 at one end adapted to fit into the collet 11. At the other end the shaft 51 carries the hub 53 of a bevel gear 54 meshing with the shoulder 56 in the casing, which prevents axial movement of the bearing sleeve. The hub 53 is secured on the drive shaft 51 by a pin 57, so gear thrust is transmitted from the hub 53 to the end of the bearing sleeve 48.

In the normal operation of this structure, assembled as shown, rotation of the collet 11 causes a corresponding rotation of the drive shaft 51 and through the bevel gears 54 and 41 rotates the hub 38 so that the tool 47 is similarly rotated. End pressure against the tool 47 is transmitted to the hub 38 and causes the end of the bevel gear hub 38 to transmit the thrust to the upper housing shell 16.

When the interior of this structure gets contaminated or if there is difficulty with bearing wear and the like, the user can unscrew the prophy head and back it away from the end of the casing 6 at the same time pulling the shaft 51 from the collet 11. When that is done the upper shell 16 and the lower shell 17 can be pulled from the snugly fitting bearing sleeve and separated from each other. The shaft 51 can be pulled from the bearing sleeve 48, thus removing the shaft and the gear 54 simultaneously. The gear 54 can be detached from the shaft by pulling the pin 57. The hub 38 can be withdrawn from the pin 26. The unit is thus entirely disassembled. It can be cleaned or lubricated or parts can be replaced, such as the hub and bevel gear 41 or the bearing sleeve 48 or the shaft 51 with the gear 54. Grease introduced into the hollow pin 26 is squeezed out to surround the pin and partly escape over the top of the hub 38 into the compartment 36 to lubricate the gears when the shank of the prophy cup is screwed into the hub 38 and enters the pin 26.

A reassembly can then be made of the various parts, and the two halves 16 and 17 can be pressed onto the bearing sleeve 48, thus holding the parts against relative axial shifting and in proper alignment. The entire head can again be screwed into threaded engagement with the casing 6, thus locking the parts against axial shifting and lateral displacement. The prophy angle head is then available for further use until it is worn out and is discarded.

What is claimed is:

1. A prophylactic angle head for a dental handpiece comprising an upper housing shell having a planar face and having a first end portion enclosing an upper half-chamber and having a first shank portion enclosing an upper half-tube, a lower housing shell having a planar face and having a second end portion enclosing a lower half-chamber and having a second shank portion enclosing a lower half-tube, means for holding said upper housing shell and said lower housing shell with said planar faces in abutment and with said half-chambers and said half-tubes facing each other, a bearing sleeve in said half-tubes and substantially abutting said shells, a stationary journal pin fixed in said first end portion and extending through said upper half-chamber and substantially through said lower half-chamber, a hollow gear hub rotatably mounted on said pin and extending substantially through said upper half-chamber and said lower half-chamber, a first bevel gear fast on said gear hub, a shaft extending through said bearing sleeve, and a second bevel gear fast on said shaft and engaging said first bevel gear.

2. A device as in claim 1 in which said second end portion has an opening therein disposed to surround a portion of said gear hub, and in which said hub is adapted to receive a prophylactic tool.

3. A device as in claim 1 including means for preventing axial movement of said bearing sleeve along said first axis.

4. A device as in claim 1 including a shoulder on said journal pin abutting one side of said upper half-chamber, and including a riveted cap on said journal pin abutting the other side of said upper half-chamber.

5. A device as in claim 1 in which said journal pin is hollow, and including threads on said gear hub in position to engage threads on a dental tool extending into said hollow journal pin.

* * * * *